United States Patent

Poliac

[11] Patent Number: 5,720,292
[45] Date of Patent: Feb. 24, 1998

[54] BEAT ONSET DETECTOR

[75] Inventor: Marius O. Poliac, St. Paul, Minn.

[73] Assignee: Medwave, Inc., Arden Hills, Minn.

[21] Appl. No.: 690,627

[22] Filed: Jul. 31, 1996

[51] Int. Cl.$^6$ .......................................... A61B 5/02
[52] U.S. Cl. ........................................ 128/672; 128/687
[58] Field of Search ............................ 128/668, 672, 128/687, 688, 689, 690

[56] References Cited

U.S. PATENT DOCUMENTS

4,418,700  12/1983  Warner .................................. 128/672
5,140,991  8/1992  Niwa ..................................... 128/687
5,406,952  4/1995  Barnes et al. .......................... 128/690
5,584,299  12/1996  Sakai et al. ........................... 128/672

*Primary Examiner*—Lee S. Cohen
*Assistant Examiner*—Eric F. Winakur

[57] ABSTRACT

A method for identifying an onset of a first heart beat includes sensing blood pressure over time to produce a plurality of blood pressure samples, each sample having a corresponding blood pressure amplitude in time, identifying a post onset point in time following an onset of the first heart beat and preceding an onset of a second heart beat, and identifying an onset of the heart beat based upon the blood pressure samples and the post onset point.

15 Claims, 5 Drawing Sheets

BEAT ONSET DETECTOR

BACKGROUND OF THE INVENTION

The present invention relates to methods for calculating blood pressure of an artery. More specifically, the present invention relates to a method for identifying an onset of a heart beat to aid in calculating the blood pressure of an artery.

Blood pressure has typically been measured by one of four basic methods: invasive, oscillometric, auscultatory and tonometric. U.S. patent application Ser. No. 08/388,751 entitled "METHOD AND APPARATUS FOR CALCULATING BLOOD PRESSURE OF AN ARTERY" and U.S. patent application Ser. No. 08/227,506 entitled "CONTINUOUS NON-INVASIVE BLOOD PRESSURE MONITORING SYSTEM" (herein incorporated by reference), both of which are assigned to Medwave, Inc., describe a novel non-invasive method for continuously measuring blood pressure without causing discomfort to a patient. The novel method involves non-invasively sensing the amplitude and shape of the blood pressure pulses within the underlying artery to create signals representing the amplitude of the sensed blood pressure pulses. Based upon the sensed signals representing the sensed amplitude and shape of the blood pressure pulses, wave shape information is determined by measuring the amplitude and shape versus time of individual cardiac cycles. Parameters derived from the sensed signals and the wave shape information are used by a microprocessor to calculate systolic, diastolic and mean blood pressures. Holddown pressure is applied to the anatomy of the patient directly above the artery. Preferably, the holddown pressure applied to the artery is increased or ramped upward as a sensor senses and detects the amplitude and shape of the blood pressure pulses with in the underlying artery. To calculate blood pressure from sensor signals representing the sensed amplitude and shape of the blood pressure pulses, it is important that the beginning or onset of heart beat be accurately identified or ascertained to enable accurate selection of parameters for use in calculating blood pressure.

Accurately detecting or ascertaining the onset of a heart beat has been extremely difficult and error prone because of the extreme variations between beats of different individuals. Use of a ramping or increasing holddown pressure further increases the difficulty of accurately detecting the onset of a heart beat. Moreover, the entire process of detecting the onset of a heart beat is additionally formidable because the onset of each heart beat must be digitally ascertained almost instantaneously from a series of blood pressure samples.

SUMMARY OF THE INVENTION

The present invention is a method for identifying an onset of a heart beat. The method of the present invention includes sensing blood pressure over time to produce a plurality of blood pressure samples. Each sample has a corresponding blood pressure amplitude and time. A post onset point in time following an onset of the first heart beat and preceding an onset of a second heart beat is identified. Using the post onset point and the blood pressure samples, the onset of the first heart beat is identified.

The post onset point is preferably a time period during which the sensed blood pressure increases at a fastest rate. Preferably, the time period during which the sensed blood pressure increases at a fastest rate is identified by generating a plurality of gain values. Each gain value represents a pressure amplitude change during a corresponding prese-

2 lected time period. The plurality of gain values are compared to identify a maximum gain value. The maximum gain value corresponds to the time period during which blood pressure increases at the fastest rate. Preferably, the step of generating a plurality of gain values includes magnifying pressure amplitude changes to generate the gain values. In addition, the step of comparing the plurality of gain values preferably involves the comparison of only positive gain values. The step of comparing gain values preferably additionally includes a step of generating an envelope threshold value representing preselected exponential decay of a previous identified maximum gain value, wherein only gain values greater than the envelope threshold value are compared. The step of comparing the plurality of gain values preferably includes comparing only gain values corresponding to time periods that succeed a time period corresponding to a previously identified maximum gain value by a selected amount of time.

The step of identifying an onset of the heart beat based upon blood pressure samples and the post onset point preferably includes the steps of generating a threshold rate of blood pressure change between a candidate sample preceding the post onset point and a blood pressure amplitude at a preceding identified onset of a preceding heart beat, generating a local rate of blood pressure change between the candidate sample and a preceding selected sample, and comparing the threshold rate and the local rate to determine whether the candidate sample constitutes the onset of the heart beat.

DETAILED DESCRIPTION OF THE PREFERRED EMBODIMENTS

Figure 1:
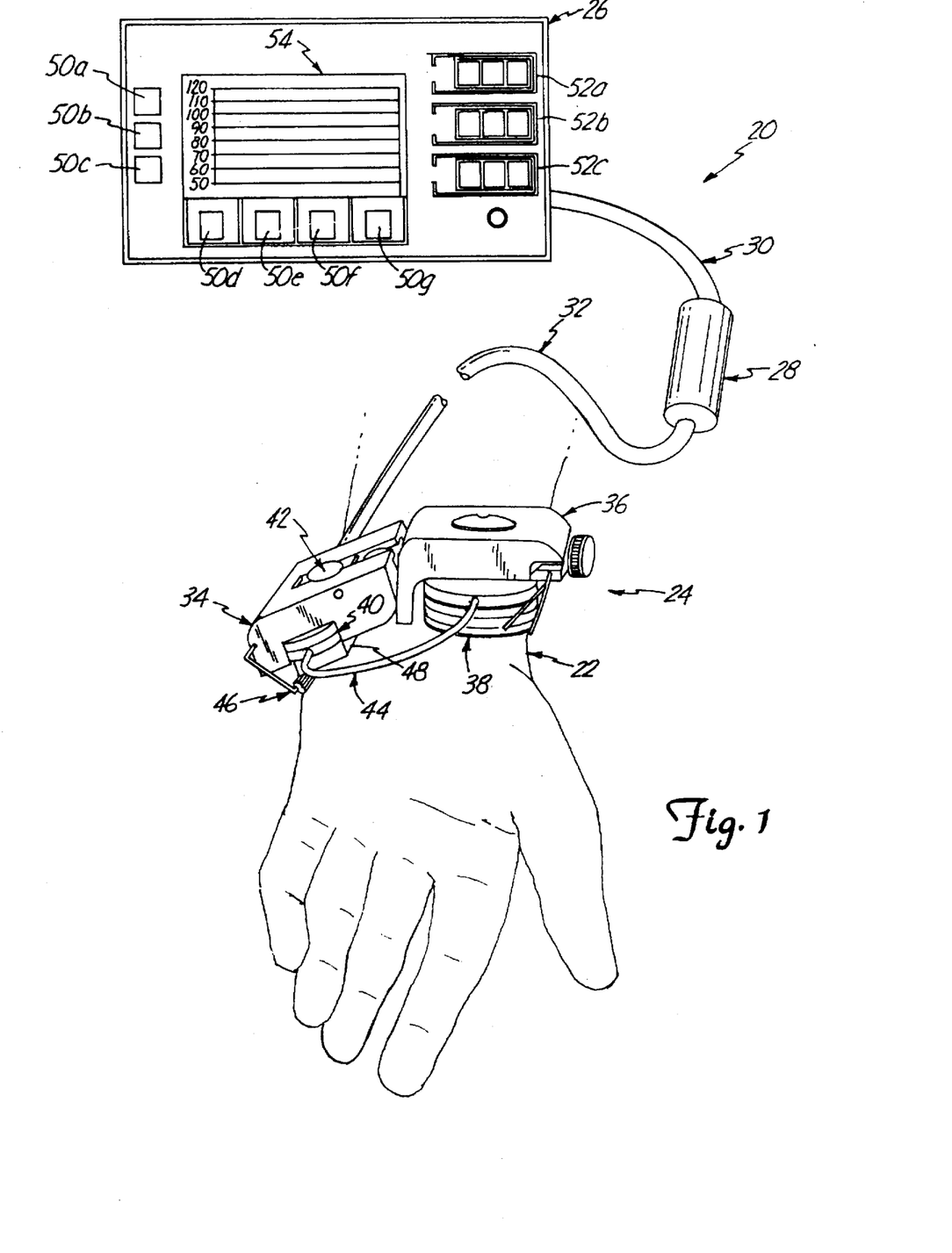
FIG. 1 is a perspective view of a blood pressure monitoring system having a sensor assembly mounted upon the wrist of a patient.

FIG. 1 illustrates blood pressure monitoring system 20 for measuring and displaying blood pressure within an underlying artery within wrist 22 of a patient. Monitoring system 20 includes wrist assembly 24, monitor 26, cylinder 28, cable 30 and cable 32.

Wrist assembly 24 is mounted on wrist 22 for applying a varying hold down pressure to an artery within wrist, and for sensing blood pressure waveforms produced in the artery. Wrist assembly 24 includes swivel mount 34, hold down assembly 36, sensor interface assembly 38, waveform pressure transducer 40, hold down pressure transducer 42, connection tube 44, wrist mount 46 and wrist pad 48.

Cylinder 28, under the control of monitor 26, supplies fluid pressure through cable 32 to wrist assembly 24 to produce the varying hold down pressure. Cylinder 28 includes a movable piston which is driven by a stopper motor or linear actuator.

Electrical energization to wrist assembly 24 and pressure waveform sensor signals to monitor 26 are supplied over electrical conductors extending between monitor 26 and wrist assembly through cable 30, cylinder 28 and cable 32. Drive signals to cylinder 28 are supplied from monitor 26 through electrical conductors within cable 30.

Monitor 26 receives the pressure waveform sensor signals from wrist assembly 24, digitizes the signals to produce pressure waveform data for a plurality of beats, and performs waveform analysis on the data. The waveform analysis extracts a plurality of waveform parameters, which preferably include waveform shape, relative amplitude and gain parameters. From the waveform parameters, monitor 26 calculates or otherwise derives blood pressure values, such as mean blood pressure, diastolic blood pressure and systolic blood pressure. Monitor 26 then displays the derived blood pressure values.

As shown in FIG. 1, monitor 26 includes control switches or input keys 50a–50g, digital displays 52a–52c and display screen 54. Input keys 50a–50c comprise hard keys for controlling monitor 32. Input keys 50d–50g consist of software programmable keys which are adaptable for various functions. Digital displays 52a–52c continually display systolic, diastolic and mean blood pressure, respectively. Display screen 54 displays the blood pressure pulse waveforms and prompts to guide the operator.

In operation, sensor interface assembly 38 is positioned over the radial artery. Wrist mount 46 maintains the position of wrist assembly 24 including sensor interface assembly 38 on wrist 22. In response to fluid pressure supplied from cylinder 28 through cable 32, hold down assembly 36 applies force and moves sensor interface assembly 38 to vary the pressure applied to wrist 22 above the radial artery.

As this pressure is varied, distinct arterial pressure waveforms are exhibited by the blood pressure pulse within the underlying artery. Each waveform corresponds to a cardiac cycle. Each arterial pressure waveform or shape is obtained by sensing and measuring pressures exhibited by the pulse of the underlying artery versus time during an individual cardiac cycle. Arterial pressure is applied to sensor interface assembly 38 and is transferred as a fluid pressure from interface assembly 38 to waveform pressure transducer 40 through tube 44. The electrical sensor signals from transducer 40 are supplied to monitor 26 for digitization and analysis.

The amplitude of each sensed waveform is a function of the pressure applied to the artery by sensor interface assembly 38 and the amplitude of the arterial pulse. The shape characteristics of at least one waveform and other parameters derived from the sensed waveforms are used by digital signal processing circuitry of monitor 26 to determine systolic, mean and diastolic pressure. The calculated pressures are displayed by displays 52a–52c and display screen 54.

Figure 2:
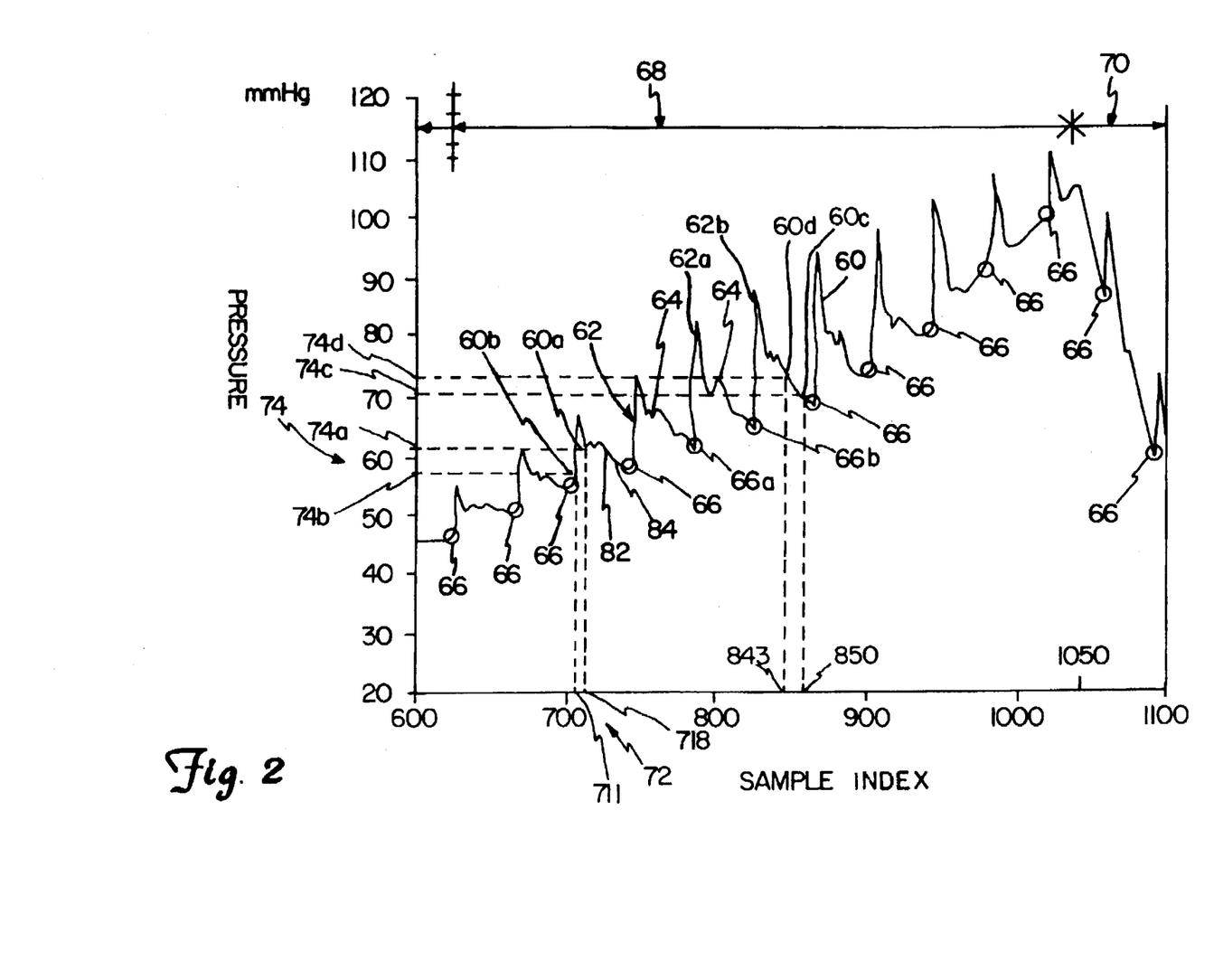
FIG. 2 is a graph illustrating a multitude of blood pressure samples sensed by the sensor assembly and digitized by the blood pressure monitoring system.

As described in U.S. patent application Ser. No. 08/388, 751, monitor 26 receives electrical signals from transducer 40 and digitizes the electrical signals for analysis to determine systolic, mean and diastolic pressure values. FIG. 2 is a graph illustrating representative blood pressure samples 60 sensed by pressure transducer 40 of wrist assembly 24 and digitized by monitor 26 (shown in FIG. 1) during a plurality of individual cardiac cycles as the pressure applied to the artery by sensor interface assembly 38 (shown in FIG. 1) is gradually increased or ramped during a ramp-up period 68 followed by a period of rapid relaxation or decreasing pressure applied to the artery by sensor interface assembly 38 during a ramp-down period 70. Preferably, monitor 26 digitizes the blood pressure sensed by pressure transducer 40 at a sampling rate of 128 pressure amplitude measurements or samples per second. Alternatively, monitor 26 may digitize blood pressure over time at a variety of sampling frequencies greater or less than the preferred sampling frequency.

As illustrated by the graph of FIG. 2, each sample 60 has a corresponding sample index number 72 representing the number of samples digitized by monitor 26 since it was started and up to the time sample 60 was taken, as indicated on the abscissa of the graph and a corresponding blood pressure value 74, expressed in mmHg, as indicated in the ordinate of the graph. As shown by the graph, the holddown pressure applied to the artery and the resulting pressure exhibited by the pulse and measured by wrist assembly 24 is gradually increased from sample index number 600 through sample index number 1050. At approximately sample index number 1050, the holddown pressure applied by wrist assembly 24 is reduced or relaxed to cause the generally downward sloping blood pressure samples. As shown in FIG. 2, blood pressure samples 60, in conjunction with one another, outline waveforms 62 which represent individual heart beats. Each waveform 62 may have one or more dichrotic notches 64. It is also possible that a waveform 62 may not include any visible sign of a dichrotic notch. As discussed above, monitor 26 derives parameters from blood pressure samples 60 and the shape characteristics of individual beats 62 to calculate systolic, diastolic and mean blood pressure. The number of dichrotic notches 64 and the general size as well as the shape of each waveform 62 vary due to varying heart rates and physical characteristics of different individuals.

To calculate blood pressure using derived parameters from blood pressure samples 60, monitor 26 preferably digitally ascertains the onset of each heart beat generally indicated by circles 66. To identify the onset of each heart beat, monitor 26 senses blood pressure over time to produce a plurality of blood pressure samples 60 and identifies a post onset point in time or "POP" following an onset of a first heart beat and preceding an onset of a second heart beat. Once the POP is identified, monitor 26 identifies the onset of the first heart beat based upon the blood pressure samples and the POP. For example, to determine the onset of a beat represented by waveform 62a, monitor 26 identifies a POP between onset 66a and 66b of waveform 62a and 62b, respectively. Once the POP is identified, monitor 26 uses the POP and the sensed blood pressure samples 60 to identify the precise location of onset 66a using the POP and the sensed blood pressure samples 60.

Figure 3:
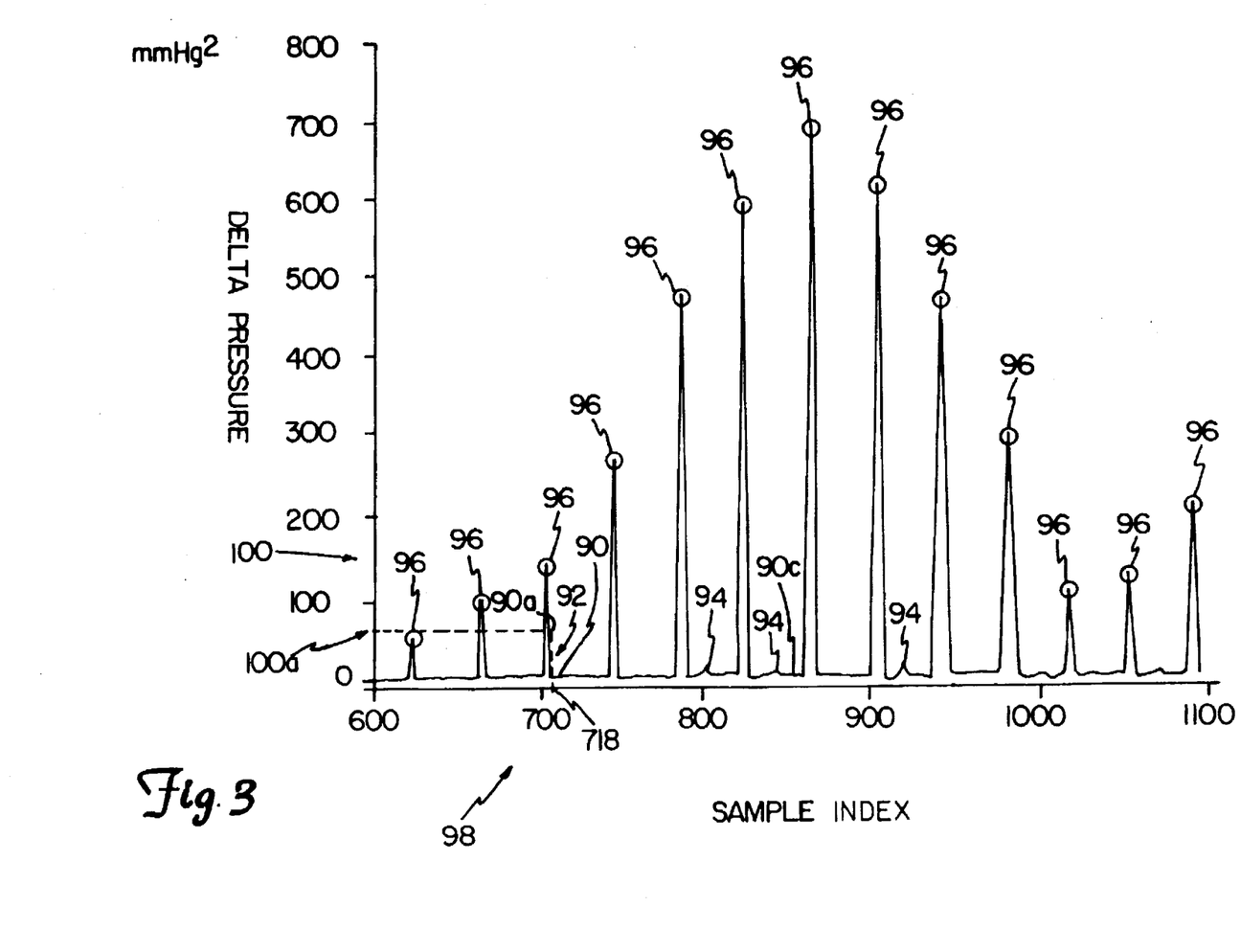
FIG. 3 is graph illustrating a multitude of delta pressure samples derived from the pressure samples of FIG. 2.
Figure 4:
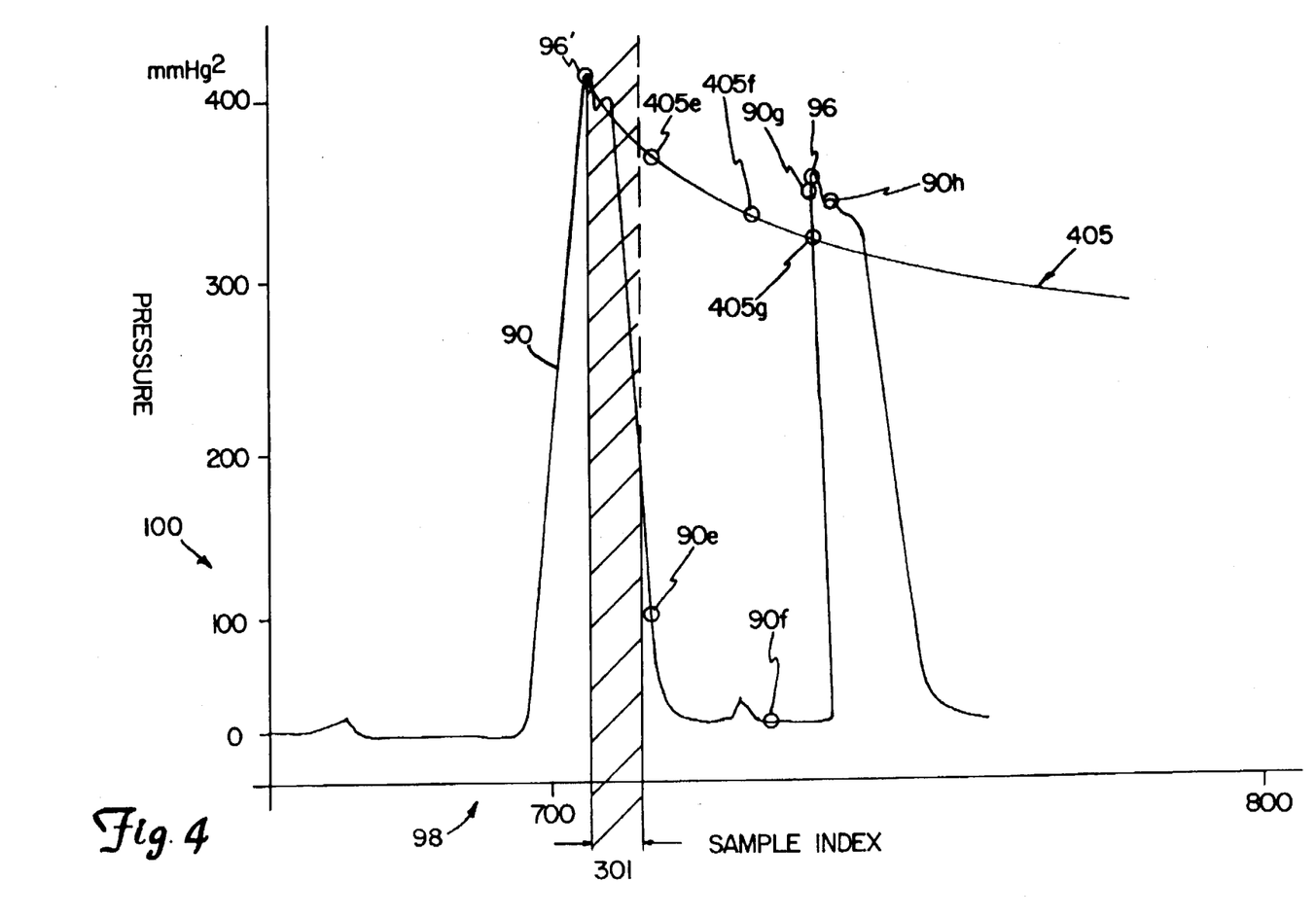
FIG. 4 is an enlarged view of a portion of the graph of FIG. 3 illustrating a method of identifying a delta pressure peak.

FIGS. 3 and 4 graphically illustrate a preferred method for identifying a POP for use in identifying an onset of a first heart beat. In particular, the preferred method of the present invention utilizes a time period during which the blood pressure increases at the fastest rate as a post onset point. FIG. 3 is a graph illustrating delta pressure samples 90 derived from blood pressure samples 60 (shown in FIG. 2). To digitally ascertain a POP for each heart beat, monitor 26 preferably transforms the blood pressure samples from FIG. 2 into a new sequence of derived delta pressure samples 90 shown in FIG. 3. For each blood pressure sample 60 (shown in FIG. 2) sensed by pressure transducer 40 and digitized by monitor 26, monitor 26 generates a delta pressure sample 90. Each delta pressure sample 90 has a corresponding sample index number 98, as indicated on the abscissa of the graph in FIG. 3 and a corresponding delta pressure value 100 expressed in $mmHg^2$, as indicated in the ordinate of the graph in FIG. 3. The sample index corresponding to delta pressure sample 90 has a corresponding sample index equal to the sample index of the corresponding blood pressure sample 60. As a result, each delta pressure sample 90 corresponds to a blood pressure sample 60 shown in FIG. 2.

To calculate a delta pressure value 100 for each delta pressure sample 90, monitor 26 compares the difference or rate of change between a preselected pair of successive blood pressure samples 60. In particular, for each first delta pressure value 90 corresponding to a first blood pressure sample 60, monitor 26 preferably compares the first blood pressure sample 60 with a second blood pressure sample 60 recorded seven samples before first blood pressure sample 60 has been recorded. If the first blood pressure sample 60 has a blood pressure value greater than the blood pressure value of the second blood pressure sample 60, monitor 26 sets the delta pressure value 100 of the first delta pressure sample 90 equal to the numerical square of the difference between the blood pressure values of the first and second blood pressure samples 60. Alternatively, if the first blood the first blood pressure sample 60 has a blood pressure value less than the blood pressure value of the second blood pressure sample 60, monitor 26 preferably sets delta pressure value 100 of the first delta pressure sample 90 at zero. In other words, monitor 26 forces the delta pressure value 100 of delta pressure sample 90 to zero if the first blood pressure sample 60 follows the second blood pressure sample 60 on a generally decreasing or down-slope region of the heart beat 62. For example, monitor 26 compares blood pressure sample 60a in FIG. 2 having sample index number 718 and blood pressure value 74a with blood pressure sample 60b having a blood pressure sample index number 711 and a blood pressure value 74b. Because blood pressure value 74a is greater than blood pressure value 74b, monitor 26 generates the numerical square of the difference between blood pressure value 74a and blood pressure value 74b to generate delta pressure sample 90a having a sample index number 718 and a delta pressure value 100a as shown in FIG. 3. To generate delta pressure value 90c, monitor 26 compares blood pressure sample 60c having a sample index number 850 and having a blood pressure value 74c with blood pressure sample 60d having a sample index number 843 and a blood pressure value 74d. Because blood pressure value 74c is less than blood pressure value 74d, monitor 26 sets delta pressure value 100 of delta pressure sample 90c at zero as shown in FIG. 3.

Because monitor 26 numerically squares any positive difference between the blood pressure values of successive blood pressure samples 60, monitor 26 magnifies and enlarges any positive difference between successive blood pressure samples 60. As a result, the relative size of each peak delta pressure sample 96 (hereinafter, delta pressure peak 96) relative to each dichrotic notch 94 is also magnified. As shown in FIG. 3, the dichrotic notch 64, if present in FIG. 2, is transformed to a reduced dichrotic notch 94. Because the value of the dichrotic notch 94 is reduced relative to the value of delta pressure peak 96, delta pressure peaks 96 are more easily identified by monitor 26 and are more easily distinguished from generally smaller peaks of each dichrotic notch 94. Thus, the likelihood of monitor 26 mistakenly identifying a dichrotic notch 94 as a delta pressure peak 96 is minimized or eliminated.

As further shown in FIG. 3, for each heart beat onset 66 depicted in FIG. 2, there is one corresponding peak delta pressure sample 96 depicted in FIG. 3. Generally, the sample index 98 corresponding to the peak delta pressure sample 96 is slightly higher than the sample index 98 corresponding to the corresponding heart beat onset 66. In other words, each beat onset 66 immediately precedes a delta pressure peak 96. It follows that the automatic detection of heart beat onsets 66 can be greatly facilitated by the automatic detection of delta pressure peaks 96.

To detect or locate a delta pressure peak 96, monitor 26 compares the delta pressure value 100 of each corresponding delta pressure sample 90 with previous delta pressure samples 90 since the most recent detected delta pressure peak 96. Although a variety of techniques may be used to identify a delta pressure peak 96, the method of the present invention combines the use of a silent period followed by a decaying exponential threshold to simplify and facilitate accurate and instantaneous detection of delta pressure peaks 96 so that the onset of each heart beat may also be accurately and instantaneously ascertained from a series of blood pressure samples. FIG. 4 is an enlarged view of a portion of FIG. 3 illustrating a multitude of delta pressure samples 90 that include a pair of consecutive delta pressure peaks 96' and 96. For purposes of discussion, the pressure peak 96' is assumed to have already been detected by monitor 26. As graphically illustrated by FIG. 4, after detecting a previous delta pressure peak 96', monitor 26 stops searching for the next peak for a duration or silent period 301 preferably equal to 15 mSecs. After the silent period 301 has passed, monitor 26 generates a variable threshold value 405 for each delta pressure sample 90. Each variable threshold value 405 is preferably an exponentially decayed value of the delta pressure value corresponding to a previously identified delta pressure peak sample 96'. Preferably, the rate of exponential decay is constant and is generally equal to −0.13 per sample assuming a sampling rate of 128 samples per second. To facilitate detection of delta pressure peak 96, monitor 26 compares the delta pressure value of each delta pressure sample 90 with its corresponding variable threshold value 405. Because the variable threshold value 405 is exponentially decayed at a constant rate of approximately −0.13 per sample, monitor 26 is able to identify delta pressure peaks 96 during both the ramp-up period 68 and the ramp-down period 70 (shown in FIG. 2) of sensor interface assembly 38 (shown in FIG. 1). As can be appreciated, the rate of exponential decay may be varied depending upon expected noise levels.

To facilitate easier detection on delta pressure peak 96, monitor 26 eliminates all delta pressure samples having a delta pressure value less than their corresponding variable threshold value 405. Once monitor 26 identifies a first delta pressure sample 90 having a delta pressure value 100 greater than its corresponding variable delta pressure threshold 405, monitor 26 compares the delta pressure value 100 of the first identified delta pressure sample to the delta pressure value of a successive second delta pressure sample 90. If the delta pressure value 100 of the first delta pressure sample is greater than the delta pressure value of the second delta pressure sample, the first delta pressure sample is identified as a delta pressure peak. However, if the delta pressure value 100 of the first delta pressure sample is less than the delta pressure value of the second delta value 100 of the second delta pressure sample, monitor 26 eliminates the first delta pressure sample as a potential delta pressure peak and proceeds by comparing the delta pressure value 100 of the second delta pressure sample with a delta pressure value 100 of a succeeding third delta pressure sample. Monitor 26 continues comparing successive pairs of delta pressure samples 90 until a first delta pressure sample having a delta pressure value 100 greater than a delta pressure value 100 of a second succeeding delta pressure sample 90 is found. Once a delta pressure sample 90 having a delta pressure value 100 greater than a delta pressure value 100 of a succeeding delta pressure sample 90 is found, the first delta pressure sample is identified as a delta pressure peak 96. For example, because the delta pressure value corresponding to delta pressure sample 90e is smaller than the variable threshold 405e, monitor 26 compares the delta pressure value of a next delta pressure sample 90f with a variable delta pressure threshold 405f. If the delta pressure value corresponding to delta pressure sample 90f is still smaller than the variable delta pressure threshold 405f, the evaluation continues until a delta pressure sample 90 is detected such that the delta pressure value corresponding to the delta pressure sample 90 is larger than the variable delta pressure threshold 405g. After detecting such a delta pressure sample 90g, monitor 26 finds delta pressure peak 96 by comparing the delta pressure value of each successive delta pressure sample 90 to the delta pressure value of a preceding delta pressure sample 90 and finding a delta pressure sample 96 such that the delta pressure value corresponding to the delta pressure sample 90h succeeding delta pressure sample 96 is smaller than the delta pressure value corresponding to delta pressure sample 96. Because monitor 26 does not compare each and every pair of consecutive delta pressure samples to identify a delta pressure peak 96, monitor 26 avoids incorrectly identifying a temporary small increase between consecutive delta pressure samples resulting from noise as a delta pressure peak 96. Consequently, monitor 26 weeds out inadvertent readings to provide more robust and more reliable detection of delta pressure peaks 96. As a result, monitor 26 is able to quickly and accurately identify delta pressure peaks 96.

Once a post onset point, preferably delta pressure peak 96, is detected by monitor 26, monitor 26 detects the corresponding heart beat onset 66 based upon blood pressure samples sensed before the post onset point (delta pressure peak 96). Monitor 26 preferably generates a value representing a threshold rate of blood pressure change between a candidate blood pressure sample preceding the post onset point (delta pressure peak 96) and a blood pressure sample identified as an onset of a preceding heart beat. Monitor 26 generates a local rate of blood pressure change between the candidate sample and a preceding preselected blood pressure sample. Monitor 26 compares the threshold rate of blood pressure change and the local rate of blood pressure change to determine whether the candidate sample constitutes the onset of the heart beat.

Figures 5, 5A:
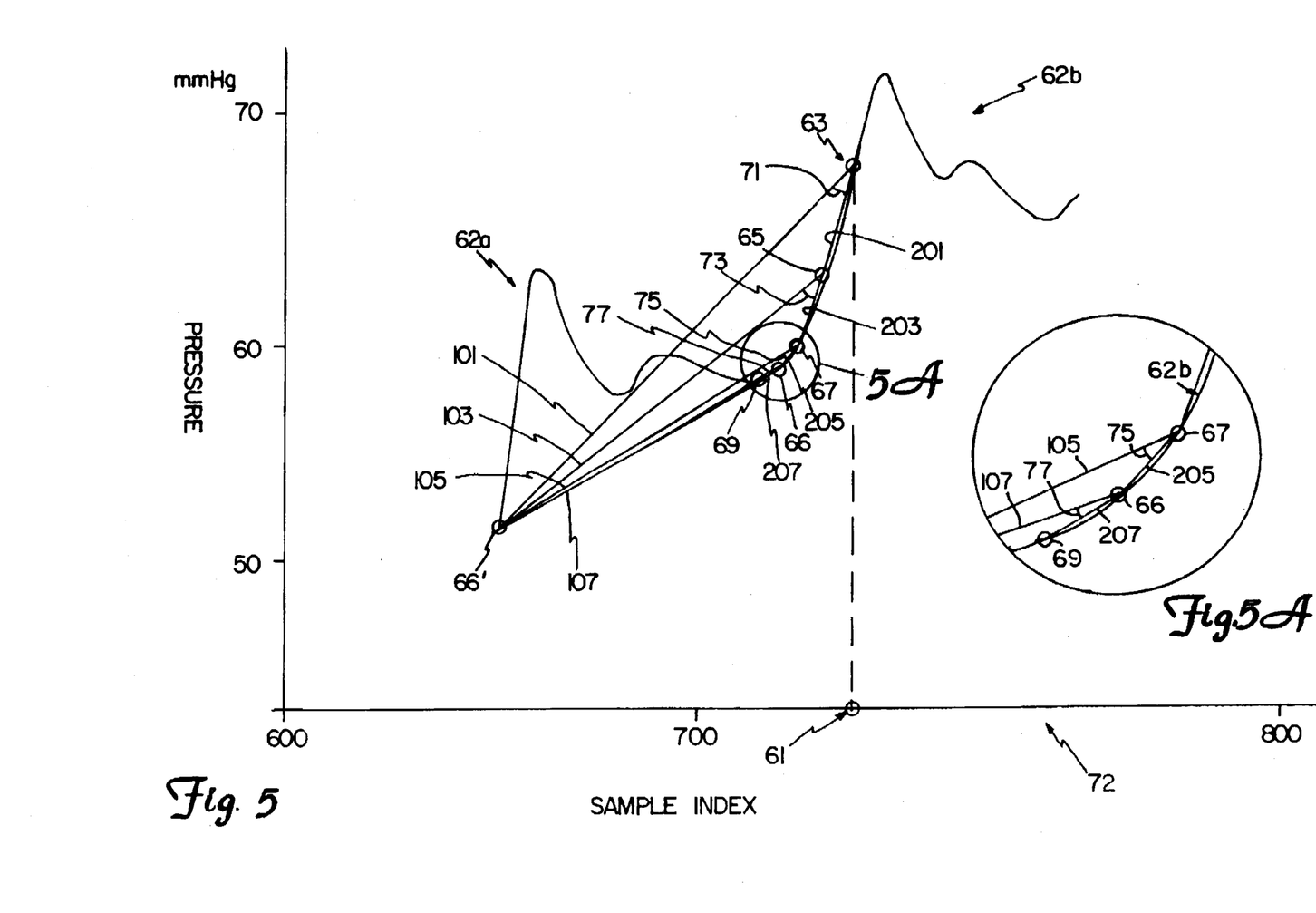
FIG. 5 is an enlarged view of a portion of the graph of FIG. 2 illustrating a method for identifying an onset of a heart beat based upon the identified delta pressure peak of FIG. 4.
FIG. 5A is an enlarged view of a circled portion of FIG. 5.

FIG. 5 and FIG. 5A are enlarged views of a portion of the graph illustrated in FIG. 2 and graphically illustrates the preferred method by which monitor 26 identifies an onset of a heart beat based upon blood pressure sample sensed before the POP, preferably delta pressure peak 96. FIG. 5 illustrates two successive waveforms 62a, 62b and a plurality of individual pressure samples 63, 65, 66, 66' and 69 of samples 60. As shown in FIG. 5, monitor 26 first selects a blood pressure sample 63 having a sample index 72 corresponding to the sample index 98 of the delta pressure peak 96 (shown in FIG. 3). Monitor 26 computes the size of angle 71 formed by segment 101 connecting blood pressure sample 63 with the previous heart beat onset 66'(presumed to have been already detected) and segment 201 connecting blood pressure sample 63 and the immediately preceding blood pressure sample 65. Monitor 26 compares the size of angle 71 with a previously set constant threshold to determine whether blood pressure sample 63 constitutes an onset of heart beat 62b. If blood pressure sample 63 is not identified as an onset of heart beat 62b, monitor 26 proceeds with the same analysis for each blood pressure sample preceding blood pressure sample 63 until the blood pressure sample is identified as an onset of heart beat 62b. For example, if blood pressure sample 63 is not identified as an onset of heart beat 62b, monitor 26 computes the size of angle 73 formed by segment 103 connecting blood pressure sample 65 with the previous heart beat onset 66' and segment 203 connecting blood pressure sample 65 and the immediately preceding blood pressure sample 67. If blood pressure sample 65 is not identified as an onset of heart beat 62b, monitor 26 continues to compute the size of such angles for each successively proceeding blood pressure samples 67, 66 and so on until a blood pressure sample having a computed angle having a preselected relationship with a previously set constant threshold is identified. In the example illustrated in FIG. 5, and FIG. 5A the sides of angle 77 formed by segment 107 connecting blood pressure sample 66 with the previous heart beat onset 66' and segment 207 connecting blood pressure sample 66 and the immediately preceding blood pressure sample 69 is smaller than a previously set constant threshold. Accordingly, blood pressure sample 66 is identified by monitor 26 as the onset 66 of the heart beat. As a result, the above described method enables monitor 26 to quickly and efficiently detect the onset of a heart beat independently of the generally up-slope induced by holddown assembly 36 during the ramp-up interval 68 and independently of the generally down-slope induced by holddown assembly 36 during the ramp-down interval 70 (shown in FIG. 2). As can be appreciated, in lieu of using angles 71–77 as values representing local and threshold rates of blood pressure change and comparing angles 71–77 to identify onset 66, monitor 26 may also compute and use a variety of other values representing local and threshold rates of blood pressure change for comparison to identify onset 66. For example, the slopes of segments 101 and 201–205 may be generated and compared for identifying onset 66.

For purposes of illustration, it has been assumed that a previous heart beat onset 66' has already been detected. To detect the very first onset, an initial blood pressure sample 60 will be deemed as an onset of a previous heart beat. As a result, the identified onsets of initial heart beats during start-up may be inaccurate. Because the identification of the onset of the second heart beat relies upon the identified onset of the first heart beat and because the identification of the onset of the third heart beat relies upon the identified onset of the second heart beat, over time, the initial inaccuracies of the very first identified onset have a reduced effect on successive identified onsets. As a result, the method of the present invention is self-adjusting or self-correcting.

In conclusion, the method of the present invention accurately, reliably and almost instantaneously identifies the onsets of heart beats or waveforms generally regardless of whether holddown pressure applied to the underlying artery is constant, increasing or decreasing and regardless of whether the heart beat is a heart beat from a healthy individual, an unhealthy individual, an old individual, a young individual or even an individual on medication. The method of the present invention is capable of identifying the onset for a wide variety of heart beats having radically differently shaped waveforms. In particular, the method of the present invention enables monitor 26 to identify a post onset point or POP. Using the POP, the method of the present invention selects and utilizes only those blood pressure samples having a preselected relationship with the POP. Preferably, only blood pressure samples preceding the POP are tested as potential onsets of the heart beat. As a result, the method of the present invention utilizes a selected portion or common nucleus of each and every heart beat or waveform to consistently and accurately identify the onset of each waveform regardless of the waveform's overall shape. Because the method of the present invention identifies and utilizes only a common nucleus from each waveform to identify the onset of each waveform, the remaining portion of each waveform, regardless of shape or differences, is ignored. Because the method of the present invention rejects, ignores or otherwise discards the remainder of blood pressure samples forming each waveform, errors and inconsistencies in the identification of the onset caused by noise or blood pressure samples representing irregularly shaped or radical portions of a waveform are eliminated. As a result, the method of the present invention enables monitor 26 to detect the onset of a large variety of beats from persons that are older or younger, persons who exercise or who are passive, or persons on or off medication.

In addition, because monitor 26 identifies and utilizes only a selected important portion or common nucleus of each and every heart beat or waveform for identifying the onset of each waveform, the method of the present invention enables monitor 26 to almost instantaneously identify the onset of each heart beat from a plurality of blood pressure samples. Because the method identifies a time period during which the sensed blood pressure increases at a fastest rate, i.e., a delta pressure peak, and identifies the onset of the heart beat based upon blood pressure sample sensed before the delta pressure peak, the large portion of the blood pressure samples forming each waveform, generally unrelated to the onset, may be ignored by monitor 26 in identifying the onset of the heart beat. Because the method of the present invention compares only delta pressure samples which occur after a silent period and which have a delta pressure value greater than a generated variable threshold value, monitor 26 is able to reject or eliminate a large portion of delta pressure samples as potential delta pressure peaks. Because only positive delta pressure values are compared and because positive delta pressure values are magnified, monitor 26 automatically ignores irregular or inconsequential delta pressure samples. As a result, monitor 26 can identify the onset of the heart beat more quickly.

Furthermore, because the method of the present invention identifies the onset of the heart beat by creating a threshold rate of blood pressure change between a candidate sample and a blood pressure amplitude at a preceding identified onset of a preceding heart beat, generating a local rate of blood pressure change between the candidates sample and a preceding preselected sample and comparing the threshold rate and the local rate, the method of the present invention is able to identify the onset of the heart beat independent of whether the holddown pressure applied to the underlying artery is constant, increasing or decreasing and independent of undesired and unintended ramping of holddown pressure (noise). As a result, the method of the present invention automatically takes into account any intended or unintended increasing or decreasing of holddown pressure in the identifying of the onset of the heart beat.

Although the present invention has been described with reference to preferred embodiments, workers skilled in the art will recognize that changes may be made in form and detail without departing from the spirit and scope of the invention.

What is claimed is:

1. A method for identifying an onset of a first heart beat, the method comprising:

sensing blood pressure over time to produce a plurality of blood pressure samples;

identifying a post onset point in time following an onset of the first heart beat and preceding an onset of a second heart beat; and identifying the onset of the first heart beat based upon the blood pressure samples and the post onset point.

2. The method of claim 1 wherein the step of identifying the onset of the first heart beat includes identifying the onset of the first heart beat based upon blood pressure samples sensed before the post onset point.

3. The method of claim 1 wherein the step of identifying a post onset point includes:

identifying a time period during which the sensed blood pressure increases at a fastest rate.

4. The method of claim 3 wherein identifying a time period during which the blood pressure increases at the fastest rate includes:

generating a plurality of gain values, each gain value representing a pressure amplitude change during a corresponding preselected-time period; and comparing the plurality of gain values to identify a maximum gain value, wherein the maximum gain value corresponds to the time period during which blood pressure increases at the fastest rate.

5. The method of claim 4 wherein only positive gain values are compared.

6. The method of claim 4 wherein the step of generating a plurality of gain values includes:

magnifying the pressure amplitude change during a corresponding preselected time period to generate each gain value.

7. The method of claim 4 wherein the step of comparing the plurality of gain values includes a step of generating an envelope threshold value representing a preselected exponential decay of a previously identified maximum gain value and wherein only gain values greater than the envelope threshold value are compared.

8. The method of claim 4 wherein only gain values corresponding to time periods that succeed a time period corresponding to a previously identified maximum gain value by a selected amount of time are compared.

9. The method of claim 4 wherein the step of comparing the plurality of gain values includes:

successively comparing gain values corresponding to successive time periods until a gain value less than a preselected noise threshold value is identified.

10. The method of claim 1 wherein the step of identifying the onset of the first heart beat based upon the blood pressure samples and the post onset point includes:

selecting at least one candidate blood pressure sample as a potential onset of the heart beat based upon the post onset point;

for each candidate sample selected, generating a threshold rate of blood pressure change between the candidate sample and a blood pressure amplitude at a preceding identified onset of a preceding heart beat;

generating a local rate of blood pressure change between the candidate sample and a preceding preselected sample; and comparing a threshold rate and the local rate to determine whether the candidate sample constitutes the onset of the heart beat.

11. The method of claim 1 wherein the step of identifying the onset of the first heart beat based upon the blood pressure samples and the post onset point includes:

(a) selecting a candidate blood pressure sample sensed before the post onset point as a potential onset of the heart beat;

(b) generating a threshold rate of blood pressure change between the candidate sample and a blood pressure amplitude at a preceding identified onset of a preceding heart beat;

(c) generating a local rate of blood pressure change between the candidate sample and a preceding preselected sample; and (d) comparing the threshold rate and the local rate to determine whether the candidate sample constitutes the onset of the heart beat.

12. The method of claim 11 including:

iteritively repeating steps (a)–(d) for each consecutively preceding candidate blood pressure sample until a candidate sample is identified as the onset of the heart beat.

13. A method for identifying an onset of a heart beat, the method comprising:

sensing blood pressure over time to produce a plurality of blood pressure samples, each sample representing a blood pressure amplitude at a corresponding time;

selecting at least one candidate blood pressure sample as a potential onset of the heart beat;

for each candidate sample, generating a threshold rate of blood pressure change between the candidate sample and a blood pressure amplitude at a preceding identified onset of a preceding heart beat;

generating a local rate of blood pressure change between the candidate sample and a preceding preselected sample; and comparing the threshold rate and the local rate to determine whether the candidate sample constitutes the onset of the heart beat.

14. A method for identifying an onset of a first heart beat, the method comprising:

sensing blood pressure over time to produce a plurality of blood pressure samples;

identifying a post onset point in time following an onset of the first heart beat and preceding an onset of a second heart beat, wherein the step of identifying a post onset point in time includes:

generating a plurality of gain values, each gain value representing a pressure amplitude change during a corresponding preselected time period; and comparing the plurality of gain values to identify a maximum gain value, wherein the maximum gain value corresponds to the post onset point; and identifying the onset of the first heart beat based upon blood pressure samples sensed before the post onset point by:

(a) selecting a candidate blood pressure sample preceding the post onset point as a potential onset of the heart beat;

(b) generating a threshold rate of blood pressure change between the candidate sample and a blood pressure amplitude at a preceding identified onset of a preceding heart beat;

(c) generating a local rate of blood pressure change between the candidate sample and a preceding preselected sample; and (d) comparing a threshold rate and the local rate to determine whether the candidate sample constitutes the onset of the heart beat.

15. The method of claim 14 wherein the step of identifying the onset includes:

iteritively repeating steps (a)–(d) for each consecutively preceding candidate sample until the onset of the heart beat is identified.

* * * * *

UNITED STATES PATENT AND TRADEMARK OFFICE
CERTIFICATE OF CORRECTION

PATENT NO. : 5,720,292
DATED : FEBRUARY 24, 1998
INVENTOR(S) : MARIUS O. POLIAC

It is certified that error appears in the above-identified patent and that said Letters Patent is hereby corrected as shown below:

Col. 3, line 23, delete "50a-50ccomprise", insert --50a-50c comprise--

Col. 5, lines 23-24, delete "the first blood the first blood", insert --the first blood--

Col. 5, line 34, delete "74awith", insert --74a with--

Col. 7, line 62, delete "66'(presumed", insert --66' (presumed--

Col. 10, line 21, delete "preselected-time", insert --preselected time--

Signed and Sealed this

Twenty-second Day of June, 1999

Attest:

Q. TODD DICKINSON

Attesting Officer

Acting Commissioner of Patents and Trademarks